United States Patent [19]

Eggenschwiler et al.

[11] Patent Number: 4,620,322

[45] Date of Patent: Nov. 4, 1986

[54] ELECTRO-OPTIC WELDING LENS ASSEMBLY

[75] Inventors: André M. Eggenschwiler, Obere Bühlstrasse 15, CH-8700 Küsnacht; Rolf Bruhin, Wetzikon, both of Switzerland

[73] Assignee: André M. Eggenschwiler, Küsnacht, Switzerland

[21] Appl. No.: 450,382

[22] Filed: Dec. 16, 1982

[30] Foreign Application Priority Data

Apr. 17, 1982 [CH] Switzerland .................. 2264/82

[51] Int. Cl.[4] .............................................. A61F 9/06
[52] U.S. Cl. ...................................... 2/8; 350/331 R
[58] Field of Search ................... 2/8, 432; 350/331 R, 350/335, 374; 219/147

[56] References Cited

U.S. PATENT DOCUMENTS

| | | | |
|---|---|---|---|
| 3,873,804 | 3/1975 | Gordon | 2/8 X |
| 4,039,254 | 8/1977 | Harsch | 2/8 X |
| 4,071,912 | 2/1978 | Budmiger | 2/8 |
| 4,130,903 | 12/1978 | Van Den Berg et al. | 2/8 |
| 4,155,122 | 5/1979 | Budmiger | 2/8 |

FOREIGN PATENT DOCUMENTS

| | | | |
|---|---|---|---|
| 2442998 | 3/1976 | Fed. Rep. of Germany | 2/8 |
| 2913571 | 12/1979 | Fed. Rep. of Germany | 2/8 |

*Primary Examiner*—Peter Nerbun

[57] ABSTRACT

An electro-optic welding lens assembly for the use in a welder's helmet or protective eyeshield comprises a filter arrangement with at least one liquid crystal light shutter element and a control unit for changing the transmission rate of the filter assembly in response to ambient light conditions. The light sensing element used to control the transmission of light through the filter arrangement is simultaneously an opto-electric transducer, supplying power to the control unit and the light shutter element. Thereby, there is no need for an additional power supply like a battery. If the sensing and transducer element is arranged behind the light shutter element, a self-regulating loop can be realized to continuously vary the transmission rate of the filter arrangement and thereby to keep the viewing illumination through the lens assembly essentially constant.

4 Claims, 5 Drawing Figures

ELECTRO-OPTIC WELDING LENS ASSEMBLY

FIELD OF THE INVENTION

The present invention relates to an electro-optic welding lens assembly useful in a welder's helmet or a protective eyeshield to protect the eyes of a welder against the glare of a welding arc or welding flame.

BACKGROUND OF THE INVENTION

It is well known that an extremely bright light, rich in ultraviolet and infrared rays, is produced by welding, either in gas welding as well as in electric-arc welding. Prolonged exposure to such light rays may be very harmful to the welder's eyes. It is therefore common practice that welders use a helmet with a protective filter arranged before his eyes or a protective shield comprising a protective filter and manually held in place between the welder's eyes and the welding arc or flame.

A basic problem with such protective means is that the visible light is also greatly attenuated, making it difficult for the welder to see the field of work at the beginning of the welding procedure or after having finished it.

PRIOR ART

In U.S. Pat. No. 3,873,804, a welder's helmet is disclosed which uses a liquid crystal light shutter assembly as a protective filter. The combination of such liquid crystal light shutter with two polarizing filter elements, one before and one behind the shutter element, offers the possibility to change the rate of light transmission through the filter assembly by applying an electrical field across the liquid crystal material of the light shutter. For further details, reference is made to the above mentioned U.S. Pat. No. 3,873,804.

An even better filtering may be achieved by a lens assembly as disclosed in U.S. Pat. No. 4,039,254. There is provided a protective lens assembly incorporating a liquid crystal light shutter for a welding helmet wherein two or more liquid crystal light shutters and at least three polarizers are used alternately in tandem to achieve a maximum light transmission of about 0.01% during the time the lens assembly is activated.

A number of similar protective lens assemblies are known, e.g. as disclosed in U.S. Pat. Nos. 4,039,803, 4,071,912 and 4,155,122, but all these known devices have the common disadvantage that they need a battery or accumulator as a power supply for their operation. Therefore, these devices are not very reliable as the battery or accumulator may become empty during the welding work and consequently the desired protection effect becomes nearly zero. In some cases, the limited battery life may be disadvantageous, because the lens assembly will go into the state of maximal transparency, if the battery is empty, and no protective effect of the helmet or eyeshield is assured. In some other cases, the lens assembly will reach its state of minimum light transmission when the power supply fails to operate, thereby urging the welder to remove the helmet or eyeshield before and after his welding work.

A further disadvantage of the known lens assemblies lies in the fact that they can be switched only between a state of maximal light transmission and a state of minimal light transmission, no intermediate position being possible.

OBJECTS OF THE INVENTION

The object of the present invention, therefore, is to provide an electro-optic welding lens assembly for use in a welder's helmet or eyeshield which does not exhibit the disadvantages as mentioned before and which will assure reliable operation independent from a battery or like power supply means. A further object of the invention is to provide an electro-optic welding lens assembly which automatically adapts to the present ambient illumination by varying its rate of light transmission continuously between a state of minimal transmission of light rays and a state of maximal transmission of light rays. A still further object of the invention is to provide an electro-optic welding lens assembly having a higher life duration and requiring less servicing during prolonged periods of welding work.

SUMMARY OF THE INVENTION

In accordance with the present invention, there is provided an electro-optic welding lens assembly for a welder's helmet or eyeshield comprising at least one liquid crystal light shutter adapted to rotate polarized light through a 90° angle, a first polarizer arranged in front of said light shutter and a second polarizer arranged behind said light shutter, whereby both polarizers are polarized in the same direction, and a control means for generating an electrical signal connected to the light shutter and incorporating sensing means responsive to ambient light conditions. The amplitude of said electrical signal is varied in response to the amount of ambient light received by said sensing means to vary the rate of light transmission through the lens assembly. The control means further comprises an opto-electric transducer means incorporating at least one transducer member exposed to ambient light conditions and serving as a power supply for the operation of said control means.

Advantageously, said sensing means comprises at least one sensor constituted by an opto-electric transducer member of the power supply. Preferably the control means comprises a regulating loop to control the rate of light transmission through the lens assembly, incorporating at least one regulating member constituted by at least one part of the lens assembly.

These and other preferred characteristics of the electro-optic welding lens assembly can further be seen from the appended claims.

BRIEF DESCRIPTION OF THE DRAWINGS

The above and other objects and features of the present invention will become even more apparent from the following detailed description taken in connection with the accompanying drawings, in which.

Figure 1:
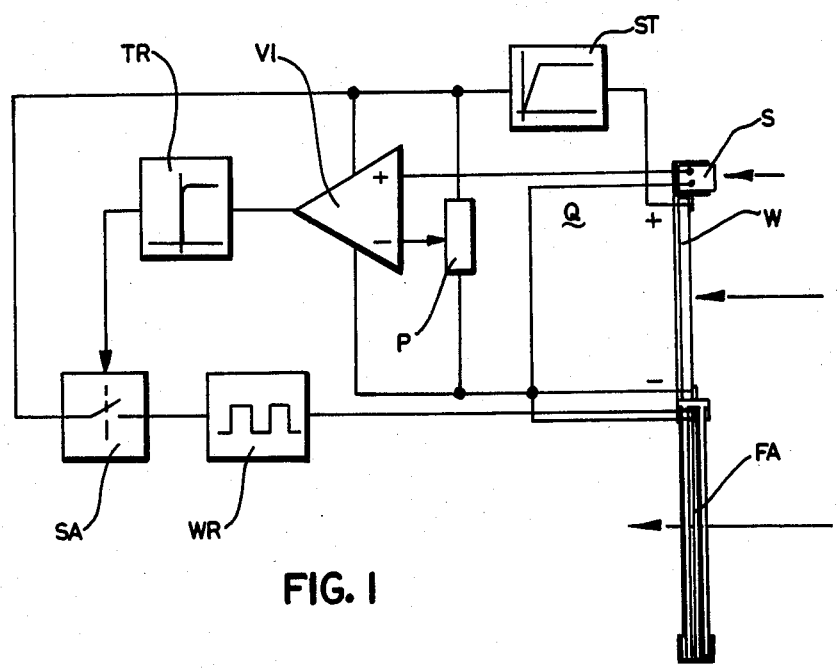
FIG. 1 shows a schematic diagram of a first embodiment.

As can be seen from FIG. 1, the first embodiment of an electro-optic welding lens assembly comprises a filter arrangment FA known per se, as disclosed e.g. in U.S. Pat. No. 4,039,254. The light transmission through the filter arrangement is influenced by a control unit which will be described in more detail hereinafter. A power supply Q is connected to the filter arrangement to provide power both to the filter arrangement and to the control unit.

The opto-electric lens assembly further comprises an opto-electric transducer element W, which is exposed to ambient light conditions, shown in the drawings by an arrow, a stabilisator circuit ST connected in series with said transducer element W and an oscillator WR. The control unit incorporates sensing means and control means to influence the transmission rate of the filter arrangement including a light sensitive element S as a sensor. A differential amplifier $V_1$ serves as a comparator circuit, whereby the positive input terminal of the amplifier $V_1$ is connected to said sensing element S and the negative input of the amplifier $V_1$ is connected to the taper of a potentiometer, furnishing a predetermined and adjustable voltage to said negative input. The power supply terminals of the amplifier $V_1$ are connected via stabilisator circuit ST to the transducer element W which delivers electrical energy in response to the ambient light falling onto said transducer element. The output terminal of the amplifier $V_1$ is connected to a trigger circuit TR, which itself is connected to the control terminal of an analog switch circuit SA. The switched terminals of the latter are in series with the power supply circuit Q providing the control signal to the liquid crystal light shutter element within the filter arrangment FA. A lens assembly as just described is independent from a separate power supply means like a battery, works very reliably and is exactly adjustable with respect of the switching threshold.

Figure 2:
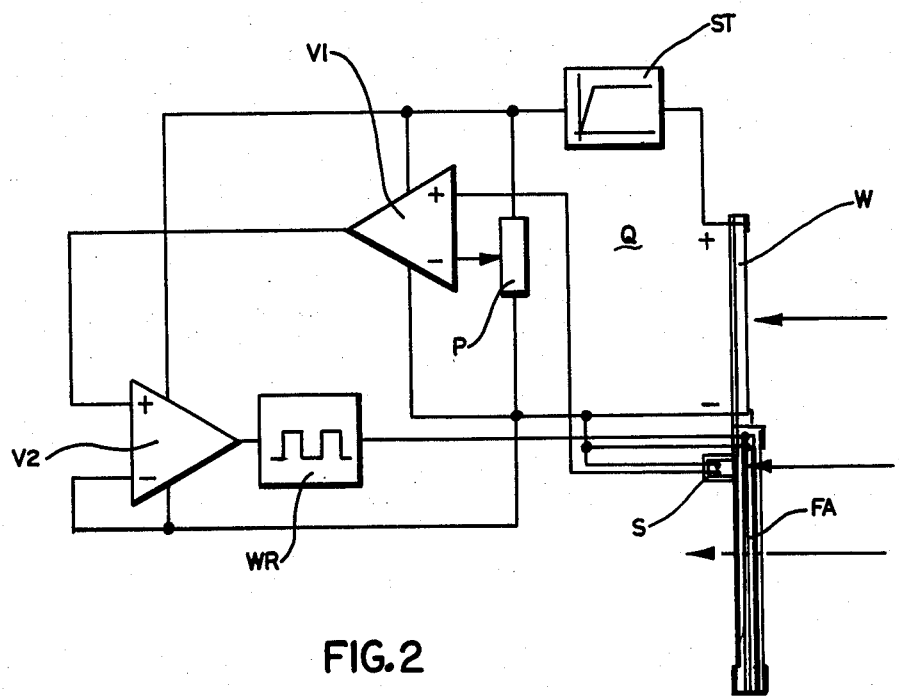
FIG. 2 shows a schematic diagram of a second embodiment.

In a second embodiment shown in FIG. 2, the sensing element S is arranged behind the filter arrangement FA, viewed in the direction of entering light rays (arrow). Thereby, a regulating loop for the control of the transmission rate of the filter arrangement is realized, the regulating member being the filter arrangement FA. The differential amplifier $V_1$ is connected as comparator similar to the embodiment shown in FIG. 1, whereby the potentiometer P sets the negative input of amplifier $V_1$ to a selectable, predetermined value. The output of the amplifier $V_1$ is connected to a power amplifier $V_2$, which drives the oscillator WR.

The remaining circuit configuration corresponds to the embodiment shown in FIG. 1.

The embodiment according to FIG. 2 provides a lens assembly with a control unit that assures that the amount of the light transmitted by the filter arrangement FA is nearly constant within certain limits. Such a lens assembly may be used in a welder's helmet or protective eyeshield and assures that the amount or intensity of light reaching the eyes of the user remains substantially constant, independent of ambient light conditions, which can vary in intensity within wide limits.

Figure 3:
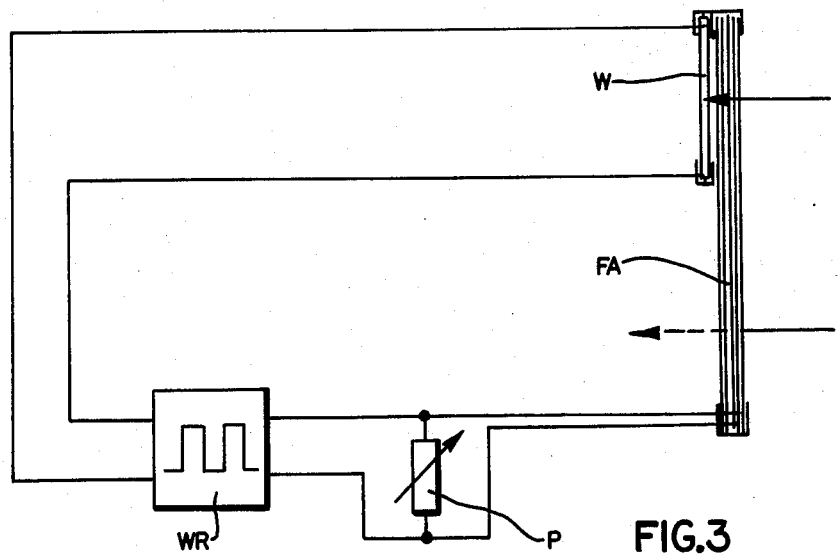
FIG. 3 shows a schematic diagram of a third, simplified embodiment.

In FIG. 3, there is shown a further embodiment which also allows a continuous control of light transmission through the filter arrangement providing an essentially constant intensity of object illumination, but being much simpler in design and requiring less parts for the control circuit. In this case, the transducer element W, which is arranged behind the filter arrangement FA in the transmitted light, simultaneously serves as opto-electric transducer for supplying power to the control circuit and as sensing member for the regulation of the transmission rate of the filter arrangement FA. The oscillator WR is connected directly to the transducer element W. As the transducer element W works with very low light intensity as long as the filter arrangement FA is in its darkened state and thereby exhibits a high internal resistance, there is provided a shunt potentiometer P for the regulation of the control circuit, which cooperates with the high impedance input of the filter arrangement.

Figure 4:
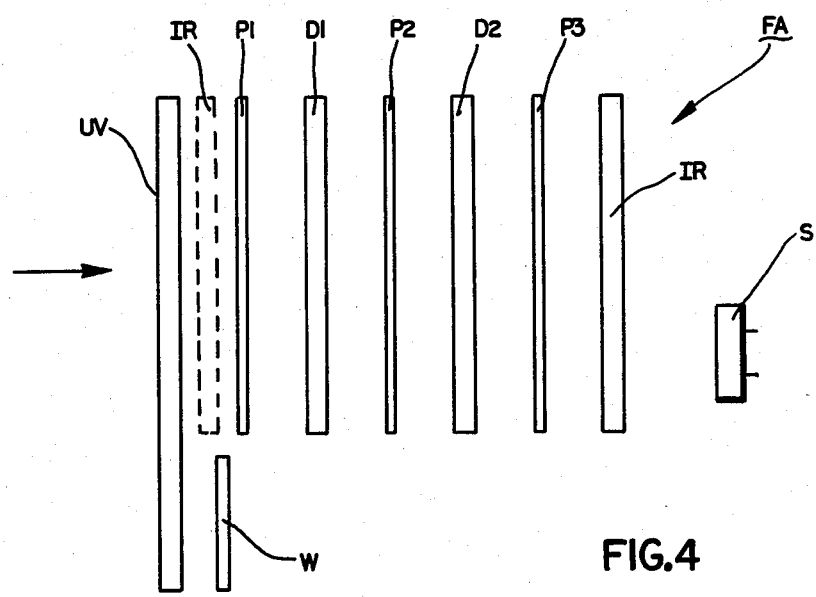
FIG. 4 schematically shows a side elevation of the lens assembly, in a first embodiment.

In FIG. 4, there is schematically shown a side elevation of a filter arrangement FA with parallel-connected transducer element W and series-connected sensing element S. It is understood that the representation shown in FIG. 4 is widely spread for clarity's sake; in fact, the filter elements are arranged tightly together. It can be seen from FIG. 4 that the transducer element W is arranged behind an ultraviolet filter element UV. This enables the transducer element W to be operated with the utmost efficiency, taking into account its sensitivity spectrum. On the other end of the path of rays shown by the arrow in FIG. 4, there is provided an infrared filter element IR, providing a heat shield for the user of the lens assembly. Another possibility is to arrange the infrared filter element IR just behind the ultraviolet filter element UV, i.e. in front of the filter arrangement FA, as it is shown by broken lines in FIG. 4. In a well known manner, the filter arrangement incorporates two light shutter elements $D_1$ and $D_2$ one behind the other one as well as three polarizers $P_1$ to $P_3$.

Figure 5:
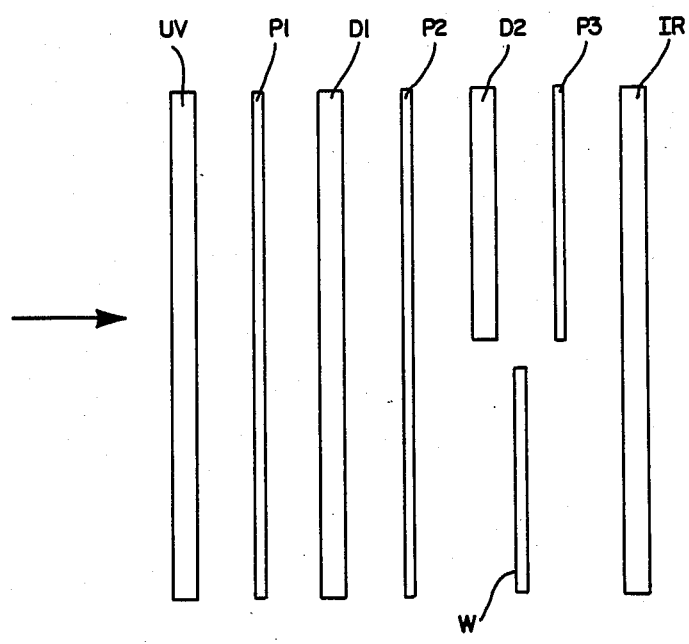
FIG. 5 shows a side elevation of the lens assembly in a second embodiment.

The embodiment according to FIG. 5 also incorporates, as shown in FIG. 4, two light shutter elements $D_1$ and $D_2$. However, the transducer element W, acting simultaneously as a sensing element for the control circuit and a opto-electric power supply transducer, is arranged behind only one of the light shutter elements $D_1$. Consequently, it is exposed to a greater light intensity when the lens assembly is in its darkened state and therefore works with greater reliability.

What we claim is:

1. An electro-optic welding legs assembly for use in a welder's helmet or protective eyeshield, said assembly comprising:
light shutter means having a variable light transmission characteristic responsive to an electrical control signal having a variable amplitude;
first polarizer means mounted in front of said light shutter means;
second polarizer means mounted behind said light shutter means, both said first and second polarizer means being polarized in the same direction; and
control means for generating said electrical control signal, said control means being connected to said light shutter means and including opto-electric transducer means for simultaneously (i) generating a signal responsive to the ambient light conditions and (ii) providing operating power to said control means, the amplitude of said electrical control signal from said control means varying said light transmission characteristic of said light shutter means in response to the signal generated by said opto-electric transducer means thereby controlling the rate of light transmission through the combination of said first polarizer means, said light shutter means, and said second polarizer means.

2. An electro-optic welding lens assembly for use in a welder's helmet or protective eyeshield, said assembly comprising:
light shutter means having a variable light transmission characteristic responsive to an electrical control signal having a variable amplitude;

first polarizer means mounted in front of said light shutter means;

second polarizer means mounted behind said light shutter means, both said first and second polarizer means being polarized in the same direction; and control means for generating said electrical control signal, said control means being connected to said light shutter means and including opto-electric transducer means positioned behind said light shutter means for simultaneously (i) generating a signal responsive to the ambient light conditions and (ii) providing operating power to said control means, the amplitude of said electrical control signal from said control means varying said light transmission characteristic of said light shutter means in response to the signal generated by said opto-electric transducer means thereby controlling the rate of light transmission through the combination of said light polarizer means, said light shutter means, and said second polarizer means.

3. An electro-optic welding lens assembly for use in a welder's helmet or protective eyeshield, said assembly comprising:

light shutter means having a variable light transmission characteristic responsive to an electrical control signal having a variable amplitude;

first polarizer means mounted in front of said light shutter means;

second polarizer means mounted behind said light shutter means, both said first and second polarizer means being polarized in the same direction;

an ultraviolet filter element transparent for infrared rays;

an infrared filter element transparent for ultraviolet rays, both said ultraviolet filter element and said infrared element mounted in line with said light shutter means; and control means for generating said electrical control signal, said control means being connected to said light shutter means and including opto-electric transducer means positioned behind said ultraviolet and infrared filters and said light shutter means for simultaneously (i) generating a signal responsive to the ambient light conditions and (ii) providing operating power of said control means, the amplitude of said electrical control signal from said control means varying said light transmission characteristic of said light shutter means in response to the signal generated by said opto-electric transducer means thereby controlling the rate of light transmission through the combination of said first polarizer means, said light shutter means, said second polarizer means, said ultraviolet filter element, and said infrared filter element.

4. The welding lens assembly of claim 1, 2 or 3, wherein said control means further includes regulating loop circuitry adapted to control said rate of transmission of light wherein said light shutter means is part of said regulating loop circuitry.

* * * * *